United States Patent [19]
Taenzer et al.

[11] 4,065,976
[45] Jan. 3, 1978

[54] MECHANICAL SCANNING METHOD AND APPARATUS FOR ULTRASONIC IMAGING, OR THE LIKE

[75] Inventors: Jon C. Taenzer; Steven H. Johnson, both of Palo Alto, Calif.

[73] Assignee: Stanford Research Institute, Menlo Park, Calif.

[21] Appl. No.: 724,330

[22] Filed: Sept. 20, 1976

[51] Int. Cl.² ............... G01N 29/00; F16H 21/16
[52] U.S. Cl. ........................................ 73/633; 74/25
[58] Field of Search .......... 73/67.8 S, 71.5 US, 73/67.9; 74/25; 324/37

[56] References Cited
U.S. PATENT DOCUMENTS

| | | | |
|---|---|---|---|
| 3,913,388 | 10/1975 | Berner | 73/67.8 S |
| 3,921,440 | 11/1975 | Toth | 73/71.5 US |

OTHER PUBLICATIONS

Machine Design; Aronson, R; "Large Oscillation Mechanisms," vol. 32, No. 23, Nov. 10, 1960, pp. 190–197.

Primary Examiner—Richard C. Queisser
Assistant Examiner—Stephen A. Kreitman
Attorney, Agent, or Firm—Victor R. Beckman

[57] ABSTRACT

Mechanical scanning apparatus is shown which includes a parallelogram linkage comprising a pair of parallel arms and parallel first and second connecting links adjacent opposite ends of the arms pivotally connected thereto. Transducer means, such as an ultrasonic transducer or transducer array, included in the ultrasonic imaging system, or the like, are attached to said first connecting link for movement therewith. First supporting means, adjacent the arm ends opposite the transducer means, support the parallelogram linkage thereat for movement along an arcuate path which closely approximates a portion of an ellipse adjacent a focus thereof. Constraining means, intermediate the first supporting means and transducer means, limit an intermediate portion of the parallelogram linkage to generally straight line movement along a path which extends substantially along a portion of the major axis of the ellipse. Upon drive operation of the linkage the transducer means, which are located at the minor axis of the ellipse, are moved with a linear translational motion along said minor axis. The constraining means may include a third connecting link extending between the arms which link is connected to a shaft constrained to move along a straight-line path. By pivoting the shaft and attached connecting link, sector scanning motion of the transducer means is provided, and by simultaneously pivoting the connecting link and driving the upper end of the parallelogram linkage along said arcuate path, a compound linear-sector scanning transducer motion is provided.

21 Claims, 7 Drawing Figures

MECHANICAL SCANNING METHOD AND APPARATUS FOR ULTRASONIC IMAGING, OR THE LIKE

ORIGIN OF INVENTION

The invention described herein was made in the course of a contract with the Department of Health, Education and Welfare.

BACKGROUND OF THE INVENTION

Acoustic imaging means which employ mechanically scanned transducer means are well known as shown, for example in the following U.S. Pat. Nos: Klahr, 3,805,596; Rosauer, 3,547,101; Flaherty et al, 3,480,002; Spencer et al, 3,765,229; Walther, 3,585,851 and ; Clynes, 3,323,512. Some prior art arrangements are not adapted for rapid back and forth linear movement required for real-time imaging which is particularly useful in medical diagnosis. Other arrangements are bulky, take up much space, and are not readily adapted for use at different parts of the body. Still other prior art arrangements employ linear or sliding bearings which operate with higher friction than the pivoting joints employed in the present arrangement.

SUMMARY OF THE INVENTION AND OBJECTS

An object of this invention is the provision of an improved mechanical system for converting from, say, rotary to linear motion, which system may be operated for rapid back and forth motion and without the use of linear or sliding bearings.

An object of this invention in the provision of a mechanical scanning system for ultrasonic transducer means, such as a single transducer or a transducer array, which is operable in a confined space and which is readily sealed to prevent immersion, or contact, of the mechanism with the acoustic transmission liquid within which the transducer means are operated.

An object of this invention is the provision of the abovementioned type of mechanical scanning system which may be constructed without the use of linear or sliding bearings and is operable at high scanning rates without excessive wear, vibration, or the like.

The above and other objects and advantages are achieved by use of a parallelogram-type mechanism having transducer means attached to one of the parallel connecting links which pivotally connect parallel arm portions of the parallelogram. The link connecting the parallel arm members adjacent the end opposite the transducer means is supported for arcuate movement while intermediate points on the arm members are confined to substantially straight-line motion in the direction toward and away from the center of the arcuate movement whereby the transducer carrying link is moved translationally along a substantially straight-line path. For sector scanning, the intermediate arm points are interconnected by a supporting link attached to a pivotally mounted shaft which is pivoted to provide the connecting links, including the link to which the transducer means are attached, with a rocking motion. With this arrangement the rotatable connecting link shaft moves along said substantially straight-line path extending radially therefrom.

The invention, advantages thereof, and the abovementioned objects will become apparent from the following detailed description when considered with the accompanying drawings.

Figure 1:
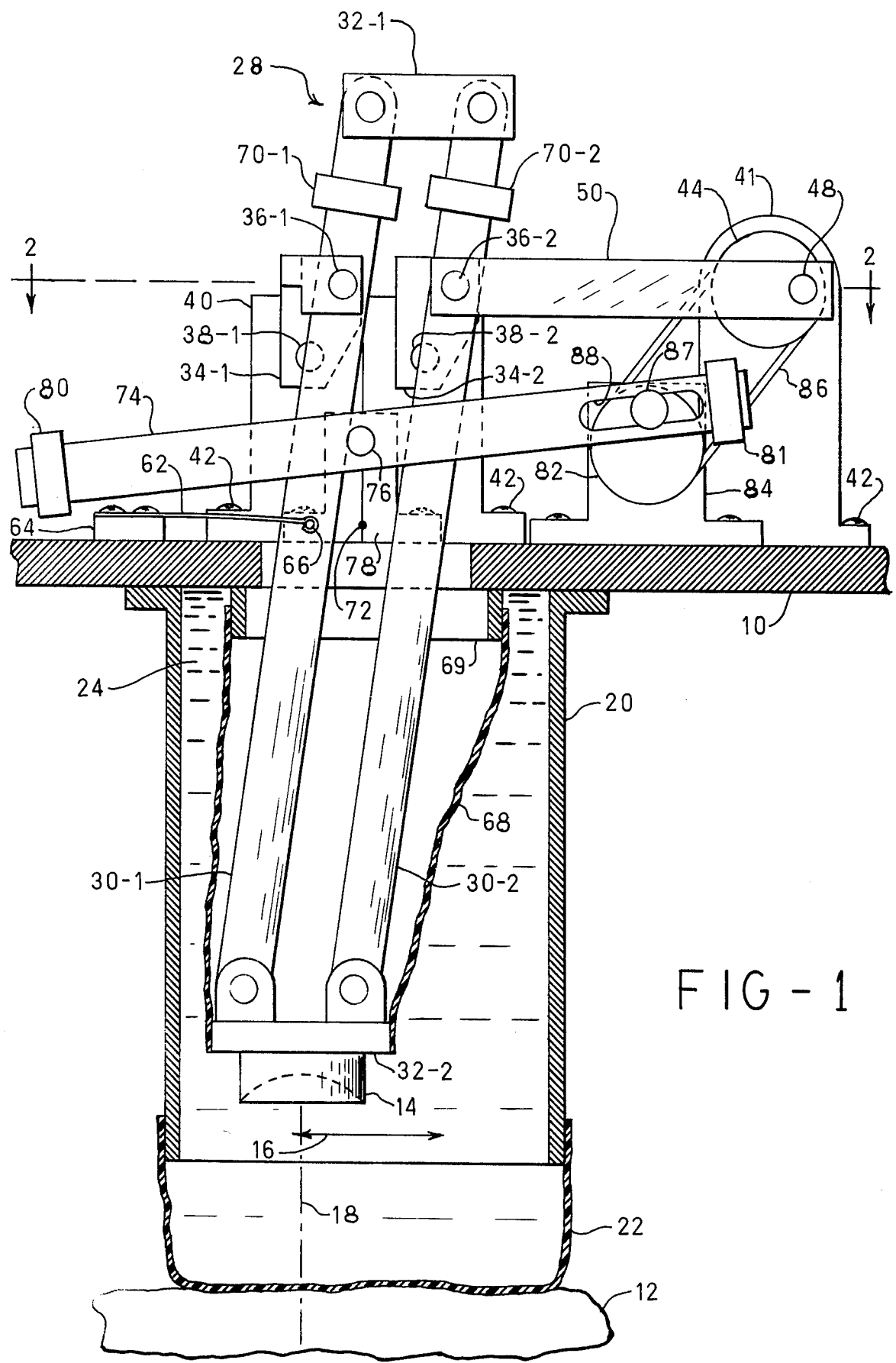
FIG. 1 is a front elevational view, with parts shown broken away for clarity, of a scanning mechanism embodying this invention.

Reference first is made to FIG. 1 wherein one embodiment of this invention is shown to include a relatively fixed support, or base plate, 10 to which the scanning mechanism is secured. In practice, the base plate 10 may be carried at the end of a movable supporting arm, not shown, for locating the mechanism at a desired position along a subject 12 under investigation. Transducer means 14, such as a single transducer or a transducer array is reciprocally moved along the direction of arrow 16 by the novel mechanical scanning system of this invention. The transducer is electrically connected to an imaging system, such as a pulsed B-scan transmitter/receiver system which may include a cathode ray tube display in which one of the orthogonal deflection voltage is proportional to the transducer position along its path of travel, the other is proportional to the time elapsed since the last transmitted pulse, and the display is intensity modulated by the received echo pulses. With such an arrangement the resulting image is of a section of the subject 12 lying on the plane of the FIG. 1 drawing along the transducer axis 18. Ultrasonic imaging systems which employ mechanically scanned transducer means are well known and require no further description for an understanding of the novel scanning mechanism.

The scanning mechanism, with the attached transducer means 14, extends into a tube 20 secured to the bottom of the base plate 10. The lower end of the tube is closed by a flexible boot 22, and the transducer means 14 is immersed in a suitable acoustic transmission medium 24, such as water, contained in the tube. Ultrasonic compressional wave pulses generated by the transducer means 14 are transmitted through the fluid medium 24 and lower end of the boot to the subject 12 along the transducer axis 18 to insonify the same, and echo signals are received from the subject through the boot and liquid medium.

In accordance with the present invention the scanning device includes a parallelogram mechanism 28 comprising parallel arms 30-1 and 30-2, together with upper and lower parallel connecting links 32-1 and 32-2, respectively, pivotally interconnecting the pair of arms. The arms 30-1 and 30-2 are supported adjacent the upper ends thereof for movement along parallel arcuate paths by equal-length supporting links 34-1 and 34-2 which are pivotally attached to the arms by pivot pins 36-1 and 36-2, respectively. The supporting links 34-1 and 34-2, in turn, are pivotally secured by pivot pins 38-1 and 38-2 to a pivot mounting block 40 attached, as by machine screws 42, to the base plate 10.

Figure 2:
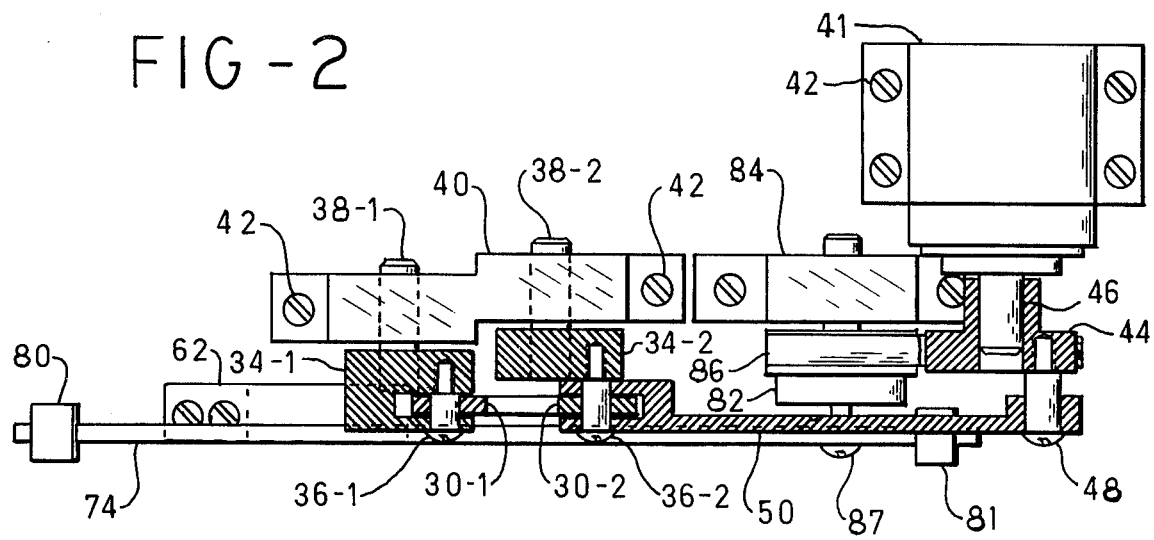
FIG. 2 is a sectional view taken along line 2—2 of FIG. 1.
Figure 3:
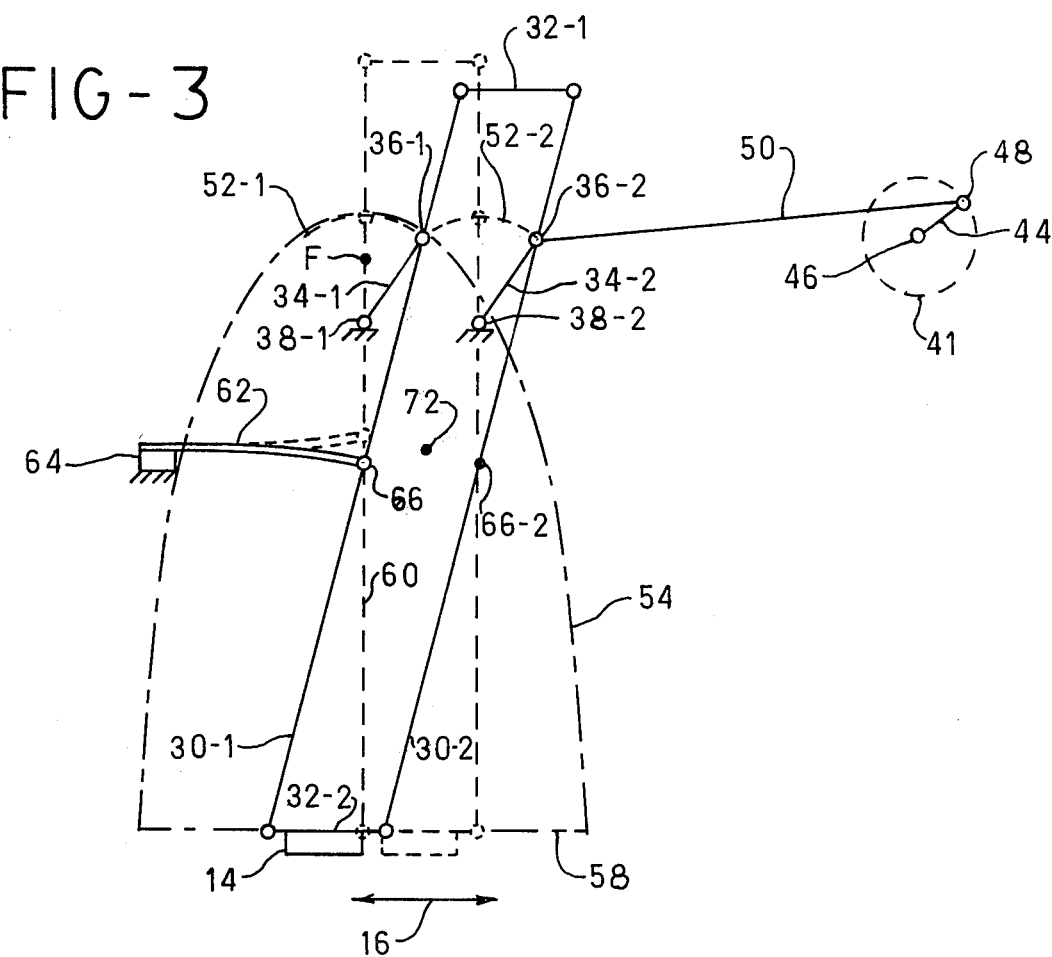
FIG. 3 is a simplified diagrammatic front elevational view of the mechanism shown in FIG. 1 without the balancing bar and associated drive mechanism therefore.

The supporting links 34-1 and 34-2, together with the attached upper end of the parallelogram mechanism 28, are rocked back and forth by operation of a drive motor 41 attached to the base plate 10 by fastening means 42 seen in FIG. 2. A combination crank disk and drive pulley 44 is fixed to the motor shaft 46. A wrist pin 48 extends from disk 44, and a drive link 50 connects the wrist pin to the pivot pin 36-2. It will be seen, then, that when the motor is energized, the supporting links 34-1 and 34-2 are pivoted about the pivot pins 38-1 and 38-2 which connect the links to the base plate through the mounting block 40. The pivot pins 36-1 and 36-2 at the other end of the pivot arms for the support of the parallelogram mechanism are moved back and forth along parallel arcuate paths identified by arrows 52-1 and 52-2 in the FIG. 3 diagram. As described below with reference to FIG. 3, the paths 52-1 and 52-2 very closely approximate portions of ellipses adjacent focii thereof. In FIG. 3 a portion of one such ellipse 54, one focus F, the minor axis 58 and a portion of the major axis 60 thereof is shown.

The parallelogram mechanism 28, intermediate the supported upper end and the transducer-carrying lower end, is constrained to move in a generally straight-line path substantially normal to the path along which the transducer means reciprocates. In the FIG. 1-4 embodiment, the constraining means comprises a leaf spring 62 having one end attached to a mounting block 64 secured to the base plate 10, and the other end pivotally attached to a pin 66 extending from opposite sides of the arm 30-1 of the parallelogram mechanism. The leaf spring, in the undeflected straight condition, extends parallel to the path of travel of the transducer means. With this arrangement although the pin 66 is constrained to move along an arcuate path, the relatively long length of leaf spring employed together with the small deflection which it undergoes as the mechanism is operated results in a substantially straight-line vertical motion of the pin 66 and attached arm 30-1 thereat. With this arrangement the use of slide bearings, or the like, to guide the pin 66 thereat is avoided.

Operation of the novel scanning mechanism will be best understood from an examination of FIG. 3, to which reference now is made. When the motor shaft 45 is rotated upon energization of the motor 41 the pivot pins 36-1 and 36-2 which are part of the parallelogram mechanism 28 are moved back and forth along paths 52-1 and 52-2 by connection thereto through the connecting arm, or rod, 50 and an eccentric which includes the disk-pulley 44 and wrist pin 48. The arcuate paths 52-1 and 52-2, comprising arcs of circles, closely follow segments of ellipses, one-half of one of which ellipses identified by reference numeral 54 is shown. As is well understood, an ellipse, adjacent its focii, closely approximates an arc of a circle. By employing relatively short path lengths 52-1 and 52-2, the paths substantially coincide with segments of the ellipses thereat.

The arm 30-1 at pivot point 66 is constrained to move substantially along the major axis 60 of the ellipse 54 by use of the leaf spring 62 connected thereto. The pin 38-1 for pivotal support of the supporting link 34-1 also is positioned on the major axis 60 of the ellipse. Consequently, it will be seen that the pin 66 is constrained to move in a direction toward and away from the mounting pin 38-1 as the mechanism is driven. A point 66-2 on the parallel arm 30-2 of the parallelogram is, of course, constrained to move along a path parallel to the pin 66. The lower connecting link 32-2, to which the transducer means 14 are attached, is located along the minor axis 58 of ellipse 54. With negligible deviation, the transducer means are translationally moved back and forth in the direction of arrow 16 upon operation of the mechanism. As seen in FIG. 1, a flexible sleeve 68 attached to the lower connecting link 32-2 at one end and a collar 69 at the bottom of the base plate at the other end, seals the fluid medium 24 inside the tube 20 and also protects the parallelogram linkage from the fluid medium 24.

Figure 4:
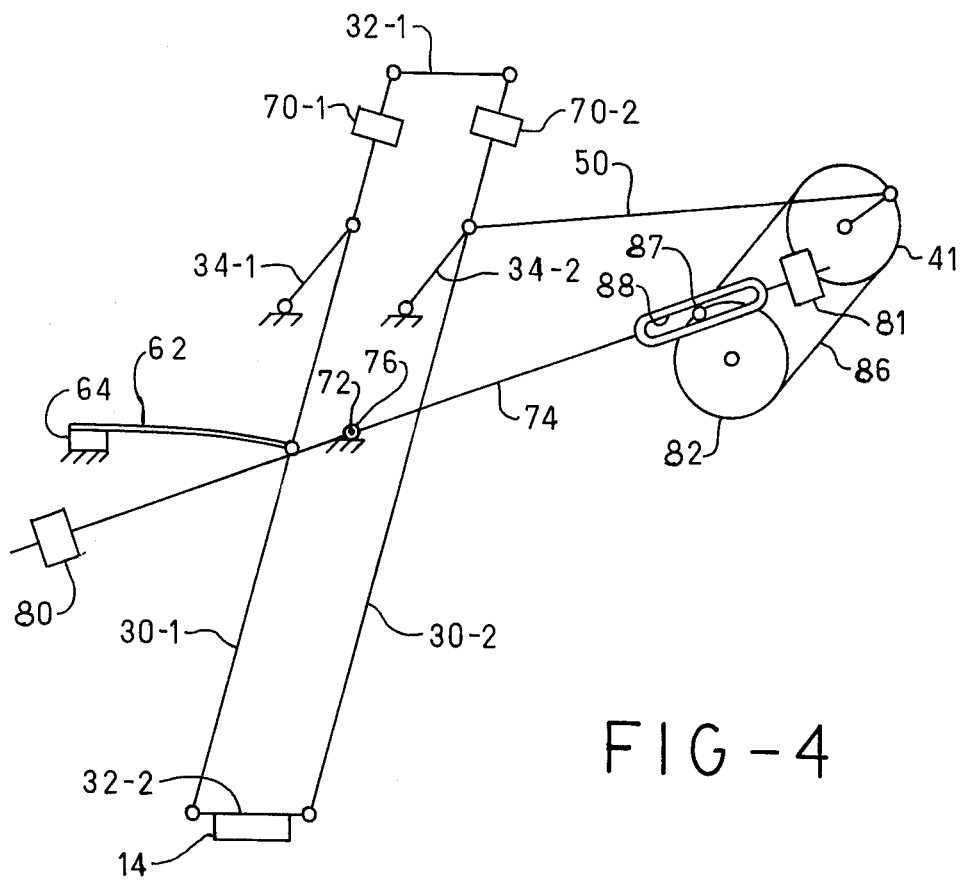
FIG. 4 is a simplified diagrammatic view which is similiar to FIG. 3, but also showing the balance bar and drive mechanism therefore.

Novel balancing means for mechanical balancing of the system include the use of weights 70-1 and 70-2 affixed to the upper ends of the arms 30-1 and 30-2 to fix the center of mass of the parallelogram linkage at a point 72 midway between the leaf spring pivot 66 and point 66-2 on the arm 30-2. Also included is a balance bar 74 pivotally supported on pivot pin 76 extending from one side of a mounting block 78 attached to the base plate 10. The pivot axis for the balance bar preferably is in alignment with the center of mass 72 (FIG. 4) of the parallelogram mechanism. However, in the arrangement shown in FIGS. 1 and 2 the balance bar pivot axis is located slightly above the center of mass, above the base plate 10. In the diagram of FIG. 4, the pivot axis and center of mass are shown aligned to illustrate the more desirable relationship therebetween. Weights 80 and 81 are secured to the outer ends of the balance bar 74.

The weighted balance bar 74 is driven at the same rate, but in an opposite direction, as the parallelogram mechanism 28. The drive means includes a pulley 82 rotatably supported on a block 84 attached to the base plate 10 and driven by the drive pulley 44 through a toothed timing belt 86. An eccentric pin 87 extends from the side of the pulley 82 for engagement with a slot 88 formed in the balance arm. It will be apparent that the balance arm is pivoted about the pin 76 by operation of the motor 41 during drive actuation of the parallelogram mechanism. By driving the balance bar 74 out of phase with the parallelogram mechanism, and by correctly choosing the size of the weights, reaction torques that are opposite and substantially equal are produced by the two systems, which torques thereby cancel. Consequently, the overall system has little residual vibration. It will be understood that serious degradation of the ultrasonic imaging system would result if vibration is not substantially removed.

Figure 5:
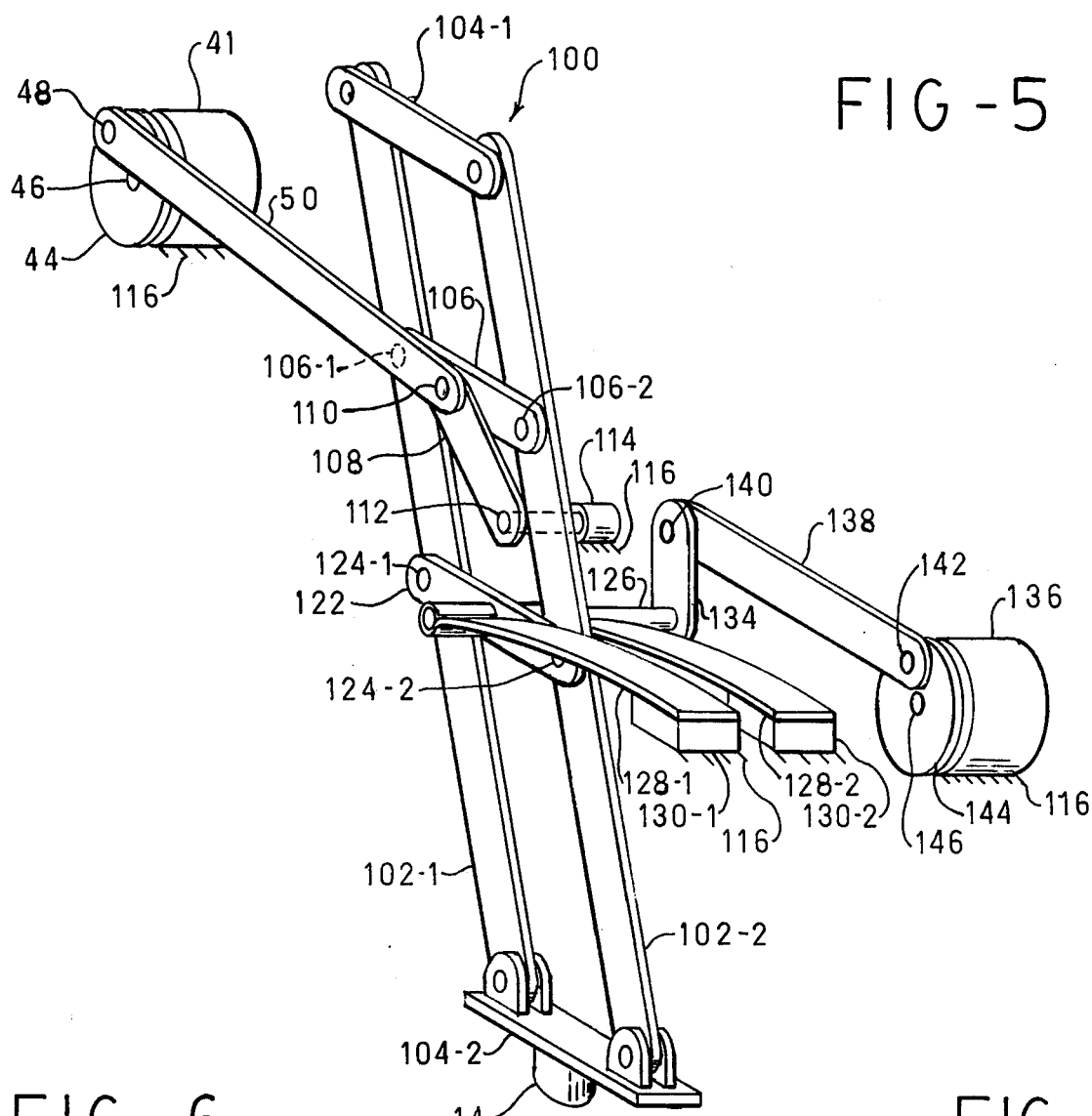
FIG. 5 is a pictorial view of a modified form of scanning mechanism which includes means for sector scanning of the transducer means.
Figure 6:
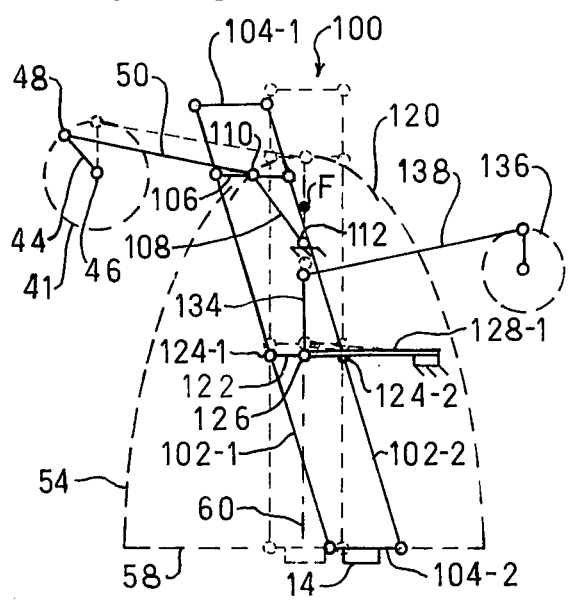
FIGS. 6 and 7 are simplified diagrammatic front elevational views of the modified form of mechanism shown in FIG. 5 for use in describing the linear and sector scanning operation, respectively, thereof.
Figure 7:
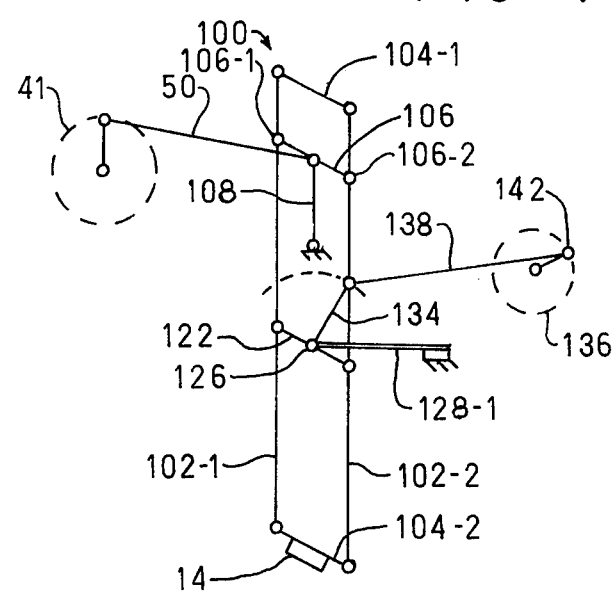

A modified form of the invention which provides also for sector scanning or combined linear and sector scanning, in addition to linear scanning of the transducer, is shown in FIGS. 5-7 of the drawings to which reference now is made. There, a parallelogram linkage 100 is shown comprising parallel arms 102-1 and 102-2 interconnected by upper and lower connecting links 104-1 and 104-2, respectively, in the manner of linkage 28 shown in FIGS. 1-4 and described above. As with the FIGS. 1-4 arrangement, transducer means 14 are attached to the lower link 104-2 for scanning movement thereof by the linkage.

The parallelogram linkage 100 is supported adjacent its upper end by a connecting link 106 pivotally attached by pivot pins 106-1 and 106-2 to the opposite arms 102-1 and 102-2 of the linkage. A pivot pin 110 extends from one side of the connecting link 106 at the center thereof for pivotal connection of the connecting link to a supporting link 108. The supporting link, in turn, is attached to a shaft 112 pivotally supported by a mounting block 114 attached to a ground or base 116.

As with the arrangement shown in FIGS. 1-4, the upper end of the parallelogram linkage 100 may be rocked back and forth by operation of the drive motor 41 connected through the crank disk 44, wrist pin 48 and drive link 50 to the pivot pin 110. It will be seen, then, that when the motor is energized the supporting link 108 is pivoted about the axis of the shaft 112 connecting the supporting link 108 to the ground member 116. The upper end of the parallelogram mechanism is thereby supported for back and forth movement along an arcuate path 120 shown in FIG. 6.

Also, as with the parallelogram linkage 28 shown in FIGS. 1-4 and described above, constraining means for constraining an intermediate portion of the linkage to movement along a generally straight-line path is provided for the modified form of invention shown in FIGS. 5-7. The constraining means comprises a connecting link 122 pivotally attached by pivot pins 124-1 and 124-2 to the opposite arms 102-1 and 102-2 of the parallelogram linkage. A shaft 126 is fixedly attached to and extends from opposite sides of the connecting link 122 midway between the pivot pins 124-1 and 124-2, which shaft is supported at the outer free ends of leaf springs 128-1 and 128-2. Shaft 126 can rotate within the ends of the leaf springs 128-1 and 128-2. The opposite ends of the leaf springs are affixed to mounting blocks 130-1 and 130-2 which, in turn, are attached to the ground, or base, plate, 116. The leaf springs, in the undeflected straight condition, extend generally parallel to the path of travel of the transducer 14. Again, as with the FIGS. 1-4 arrangement, the shaft 126 is constrained to move along an arcuate path which, in operation, closely approximates a straight-line path along the major axis 60 of the ellipse 54, because of the length of leaf springs employed and the limited deflection incurred during operation.

Referring to FIG. 6, linear scanning operation of the transducer means 14 along at least a portion of the minor axis 58 of the ellipse 54 is provided by operation of the motor 41. For this operation, connecting link 122 is held in the neutral position, shown in FIGS. 5 and 6, by the fixed attachment thereof to the shaft 126 which, in turn, is fixedly attached to a crank 134. Connecting pin 140 at the end of the crank 134 is constrained to only move vertically by means of connecting link 138, the opposite end of which pivots on pin 142 which, in turn, is held stationary directly above the shaft 146 of a motor 136 by stopping the motor in the position illustrated in FIGS. 5 and 6. The motor 136, and associated linkage is used for sector scanning, in a manner described below. When the motor shaft 46 is rotated the supporting link 108 is pivoted about the shaft 112 whereby the pivot pin 110 at the outer end thereof moves along the arcuate path 120, which path closely follows a portion of the ellipse 54 adjacent the one focus F. The shaft 126 is constrained to move along a substantially straight-line path along the major axis 60 of the ellipse by the leaf springs 128-1 and 128-2 whereby the link 104-2 supporting the transducer means 14 moves along a substantially straight-line path along the minor axis 58 of the ellipse. Such linear scan operation of the transducer means is substantially the same as for the FIGS. 1-4 mechanism and requires no further explanation.

In addition to such linear scanning motion, the parallelogram linkage 100 of FIGS. 5-7 also is adapted for sector scanning of the transducer. Sector scanning simply is provided by rocking the connecting link 122 about the axis of the attached supporting shaft 126. To this end a crank arm 134 is fixedly secured to the shaft 126 adjacent one end thereof. With the parallelogram mechanism 100 held in a rectangular neutral condition by stopping motor 41 with pin 48 directly above motor shaft 46, as shown in the broken line position thereof in FIG. 6, the crank arm 134 extends parallel with the arms 102-1 and 102-2 thereof. The crank arm 134, and attached shaft 126, may be pivoted back and forth about the shaft axis by connection of the crank arm to a second motor 136 through a connecting link 138. One end of the connecting link is connected by pivot pin 140 to the arm 134, and the other end thereof is connected to an eccentric pin 142 extending from one side of a disk 144 affixed to the motor shaft 146.

Referring now to FIG. 7, when the motor 136 is energized, connecting link 122 is pivoted about the shaft 126 axis, and the transducer is rocked about an axis extending parallel to the axes of the lower pivot pins of the parallelogram linkage, midway therebetween. As is well understood by those skilled in the ultrasonic imaging art, such sector scanning often is used instead of the above-described linear scanning motion.

Simultaneous operation of the linear and sector scanning linkages, of course, is contemplated. For example the shaft 126 may be oscillated at a high rate of operation, while the linear scanning mechanism is operated, to rock the transducer 14 rapidly while it is linearly scanned. Such transducer movement commonly is employed in medical diagnosis in order to provide insonification over a broader angle. Specularly reflecting interfaces are more likely to be detected and displayed using such combination of linear and sector scanning. Obviously, a single motor may be used for linear and sector scanning operation, if desired. Also, the arrangement may be provided with a balancing system of the type shown in FIGS. 1-4 and described above. In addition, sleeves and boots, not shown, may be used to isolate the linkage from the acoustic liquid medium within which the transducer operates in a fashion similar to that described earlier for the linear scanning linkage.

The invention having been described in detail in accordance with the requirements of the Patent Statutes various other changes and modifications will suggest themselves to those skilled in this art. For example, other mounting means for the parallelogram mechanism are contemplated. Mounting of the shaft 126 for pivotal rotation about a fixed, rather than linearly movable axis of rotation is contemplated, in which case linear scanning along an arcuate path, rather than straight-line path, would be provided. Such movement may be used independently of, or in conjunction with, the sector scanning motion. It is intended that the above and other such changes and modifications shall fall within the spirit and scope of the invention defined in the appended claims.

What is claimed is:

1. A scanning mechanism for mechanically scanning ultrasonic transducer means, or the like, comprising,
   a parallelogram linkage comprising a pair of parallel arms interconnected by a pair of parallel connecting links pivotally connected thereto,
   means for rigidly attaching transducer means to one of the connecting links, and means for driving the parallelogram linkage with relative pivotal movement of the parallel arms and connecting links in the plane of the linkage for scanning movement of the one connecting link and attached transducer means.

2. The scanning mechanism as defined in claim 1 wherein said driving means includes,
means for driving the other of said connecting links along an arcuate path, and
means for constraining the parallelogram linkage intermediate the connecting links to substantially straight line motion in the direction of the center of curvature of said arcuate path.

3. The scanning mechanism as defined in claim 2 wherein said constraining means comprises a leaf spring.

4. A scanning mechanism for mechanically scanning ultrasonic transducer means, or the like, comprising
a parallelogram linkage comprising a pair of parallel arms interconnected by a pair of parallel connecting links,
means for attaching transducer means, or the like, to one of the connecting links,
means for driving the parallelogram linkage opposite said one connecting link along a portion of an ellipse adjacent a focus thereof, and
means for constraining the parallelogram linkage intermediate the one connecting link and focus to substantially straight-line movement along a portion of the major axis of the ellipse,
said one connecting link being driven with translational movement along a straight-line path extending along the minor axis of the ellipse.

5. A mechanism for converting arcuate motion to straight line motion comprising,
an arm,
means for supporting the arm adjacent one end thereof for arcuate motion along a portion of a generally elliptical path adjacent a focus of the ellipse,
means for constraining the arm intermediate the opposite ends thereof to movement along a substantially straight line path along the major axis of the ellipse whereby the arm opposite said one end is movable along a substantially straight line path along the minor axis of the ellipse.

6. The mechanism as defined in claim 5 including,
means for oscillating said supporting means back and forth.

7. The mechanism as defined in claim 5 wherein,
said arm comprises one arm of a parallelogram mechanism which includes a second arm parallel thereto and first and second parallel connecting links pivotally connected to said arms.

8. The mechanism as defined in claim 7 wherein,
said supporting means comprise a pair of equal-length pivotally mounted supporting links pivotally attached to the parallel arms of said parallelogram mechanism for pivotal support of the arms along portions of parallel circular paths which closely approximate elliptical path portions.

9. The mechanism as defined in claim 7 wherein said constraining means comprises leaf spring means extending generally parallel to the minor axis of the ellipse,
means connecting the leaf spring to an intermediate portion of at least one of said parallelogram arms to limit movement thereat to an arcuate path which closely approximates a straight line path along the major axis of the ellipse.

10. A mechanism for converting arcuate motion to straight line motion comprising,
a parallelogram mechanism which comprises first and a second parallel arms and first and second parallel connecting links pivotally connected to said arms,
means for supporting said parallel arms adjacent one end thereof for arcuate motion along portions of generally elliptical paths adjacent focii of ellipses,
means for constraining the parallel arms intermediate the opposite ends thereof to movement along substantially straight line paths along the major axes of the elipses whereby the arms opposite said one end thereof are movable along substantially straight line paths along the minor axes of the ellipses,
weight means for establishing the center of mass of said parallelogram mechanism adjacent the constraining means where the mechanism is limited to substantially straight line motion,
a balance bar pivotally supported at a pivot axis extending adjacent the center of mass of said parallelogram, and
means for simultaneously driving said parallelogram mechanism and balance bar at the same rate but opposite rotary direction to substantially balance reaction torques produced by the resultant movements thereof.

11. The mechanism as defined in claim 7 including,
transducer means attached to said first connecting link for operation in a liquid acoustic transmission medium, and
a flexible sleeve attached to the transducer and surrounding a portion of the parallelogram mechanism for separating the mechanism from the liquid acoustic transmission medium.

12. The mechanism as defined in claim 11 including,
a tube surrounding said flexible sleeve, and
a flexible boot attached to the tube for confining the liquid acoustic transmission medium to a volume adjacent the transducer means.

13. A mechanism for converting arcuate motion to straight line motion comprising,
a parallelogram mechanism which comprises first and second parallel arms and first and second parallel connecting links pivotally connected to said arms,
means for supporting said parallel arms adjacent one end thereof for arcuate motion along portions of generally elliptical paths adjacent focii of ellipses,
means for constraining the parallel arms intermediate the opposite ends thereof to movement along substantially straight line paths along the major axes of the ellipses whereby the arms opposite said one end thereof are movable along substantially straight line paths along the minor axes of the ellipses,
said supporting means comprising a pivotally mounted supporting link pivotally attached to said first connecting link intermediate the opposite ends thereof,
said constraining means comprising a third connecting link pivotally connected to said arms parallel with and intermediate of said first and second connecting links,
a pivotally mounted shaft attached to said third connecting link intermediate the opposite ends thereof, and
said constraining means being attached to said shaft for pivotal support thereof while constraining shaft movement in a radial direction along a substantially straight line path.

14. The mechanism as defined in claim 13 including, means for pivoting said shaft and attached third connecting link about the shaft axis for pivoting said connecting links about their center points.

15. A scanning mechanism for mechanically scanning ultrasonic transducer means, or the like, comprising,
   a parallelogram linkage comprising a pair of parallel arms interconnected by first and second connecting links adjacent opposite arm ends and a third connecting link intermediate thereof,
   a supporting link pivotally attached to the first connecting link intermediate the opposite ends thereof for supporting one end of the parallelogram linkage for arcuate motion along a portion of a generally elliptical path adjacent a focus of the ellipse,
   a shaft attached to said third connecting link intermediate opposite ends and extending from opposite faces thereof,
   means for pivotally mounting said shaft including means for constraining radial shaft movement to a substantially straightline path extending along the major axis of the ellipse, and
   transducer means attached to said second connecting link at the minor axis of the ellipse.

16. The mechanism as defined in claim 15 including means for rocking said supporting link to impart a substantially straightline motion to the transducer means along the minor axis.

17. The mechanism as defined in claim 15 including means for pivoting said shaft about its rotational axis to impart a sector scanning motion to the transducer means.

18. The mechanism as defined in claim 17 including means for simultaneously rocking said supporting link to impart a combination linear and sector scanning motion to the transducer means.

19. A motion converting method employing a parallelogram linkage which includes a pair of parallel arms pivotally connected by a pair of connecting links, said method comprising
   mounting one of said connecting links, adjacent one end of the parallelogram linkage, for travel along an arcuate path which closely approximates the path of an ellipse adjacent one focus thereof, and
   constraining movement of an intermediate portion of the parallelogram linkage to substantially strainght-line movement along a path at the major axis of the ellipse for substantially straight-line motion of the parallelogram linkage adjacent the other end thereof along the minor axis of the ellipse upon movement of said one connecting link along said arcuate path.

20. The method as defined in claim 19 including,
   rocking said parallelogram linkage about an axis normal to the path of travel along the major axis of the ellipse to provide the linkage adjacent the other end thereof with a simultaneous rocking motion during movement along the minor axis of the ellipse.

21. The method as defined in claim 20 including,
   mounting transducer means at the other said connecting link for simultaneous linear and sector scanning motion thereof.

* * * * *